(12) United States Patent
Goh et al.

(10) Patent No.: US 6,513,374 B2
(45) Date of Patent: Feb. 4, 2003

(54) APPARATUS TO QUANTIFY THE ADHESION OF FILM

(75) Inventors: Loh-Nah Luona Goh, Singapore (SG); Siew-Lok Toh, Singapore (SG); Simon Chooi, Singapore (SG); Tong-Earn Tay, Singapore (SG)

(73) Assignee: Chartered Semiconductor Manufacturing Ltd., Singapore (SG)

( * ) Notice: Subject to any disclaimer, the term of this patent is extended or adjusted under 35 U.S.C. 154(b) by 35 days.

(21) Appl. No.: 09/771,512

(22) Filed: Jan. 29, 2001

(65) Prior Publication Data

US 2002/0100334 A1 Aug. 1, 2002

(51) Int. Cl.⁷ .............................. G01F 17/00; G01N 3/08
(52) U.S. Cl. ........................................ 73/150 A; 73/827
(58) Field of Search ................................ 73/150 A, 827, 73/835; 324/456, 662, 452; 156/353, 344

(56) References Cited

U.S. PATENT DOCUMENTS

| | | | | |
|---|---|---|---|---|
| 3,580,065 A | * | 5/1971 | Strittmater et al. | ....... 73/150 R |
| 3,788,135 A | * | 1/1974 | Hammond, Jr. | ............... 374/15 |
| 5,121,706 A | | 6/1992 | Nichols et al. | ............. 118/719 |
| 5,310,442 A | | 5/1994 | Ametami | ..................... 156/353 |
| 6,002,259 A | | 12/1999 | Griffin, Jr. et al. | .......... 324/456 |
| 6,370,948 B2 | * | 4/2002 | Arrington et al. | ........ 73/150 A |

* cited by examiner

Primary Examiner—Hezron Williams
Assistant Examiner—Lilybett Martir
(74) Attorney, Agent, or Firm—George O. Saile; Rosemary L. S. Pike

(57) ABSTRACT

A new apparatus is provided for the quantification of the adhesion of a film over a substrate. In particular, the peeling force and the rate of peeling are quantified by providing a first means for measuring the peeling force, a second means for measuring the rate of peeling, a third means for securing a piece of wafer, an adhesive tape, a tape holder and a resilient, flexible component.

24 Claims, 4 Drawing Sheets

APPARATUS TO QUANTIFY THE ADHESION OF FILM

BACKGROUND OF THE INVENTION (1) Field of the Invention

The invention relates to the fabrication of integrated circuit devices, and more particularly, to an apparatus to quantify the adhesion of overlying films such as dielectrics and conductors deposited on a semiconductor surface, such as the surface of a substrate.

(2) Description of the Prior Art

In the fabrication of integrated circuits, the integration of films such as dielectrics and conductors into the circuit presents a challenge. One important aspect of this integration relates to the adhesion of films (such as a film of a dielectric or a film of a conductive material) that are deposited over semiconductor surfaces such as the surface of a semiconductor substrate. In the microelectronics industry, a simple tape test, documented by the American Society for Testing and Materials (ASTM) under D3359, is typically performed to evaluate qualitatively the adhesion of a dielectric to an underlying surface. The test method teaches the placement of an adhesive tape over an area of the film, wherein the area contains a set of incisions. This is followed by the removal of the adhesive tape away from the area by seizing the free end of the tape and pulling the tape rapidly back upon itself under an angle that is as close as possible to an angle of 180 degrees.

However, this test method has several drawbacks:

(1) the test method does not provide a quantitative measurement of the adhesion between the film and the underlying surface, (2) no standards are ascribed to the several parameters that are used in this method of testing, such as the speed of pulling (removing) the tape, the type of adhesive tape that is used for the test, the pressure of rubbing the adhesive tape to the surface of the film and the force applied during the creation of the incisions in the film, (3) inconsistencies are introduced during the test, typically due to the influence of the human factor, particularly to the personality and disposition of the person that is performing the test.

The present invention therefore provides a method to quantitatively measure the adhesion of films and provides an apparatus for measuring and quantifying the adhesion between a deposited film and an underlying surface.

U.S. Pat. No. 5,310,442(Ametani) shows an apparatus for removing adhesive tape from semiconductor wafer surfaces. However, this reference differs from the apparatus of the invention.

U.S. Pat. No. 6,002,259(Griffin, Jr. et al.) teaches an electrostatic adhesion tester for thin film conductors.

U.S. Pat. No. 5,121,706(Nichols et al.) shows an apparatus for applying a composite insulating coating to a substrate. The patent discloses the D3359-83 ASTM test. Nichols et al. show an apparatus for applying coatings to substrates.

SUMMARY OF THE INVENTION

A principal objective of the invention is to provide a method and apparatus for quantifying adhesion between a deposited film, such as a film of a dielectric or a film of a conductive material, and an underlying surface.

Another objective of the invention is to provide standard measurement parameters for the measuring of the adhesion between a deposited semiconductor film of material and the underlying surface.

Yet another objective of the invention is to remove inconsistencies in quantifying adhesion between a deposited film of semiconductor material and an underlying surface.

In accordance with the objectives of the invention a new apparatus is provided for the quantification of the adhesion of a film over a substrate. In particular, the peeling force and the rate of peeling are quantified by providing a first means for measuring the peeling force, a second means for measuring the rate of peeling, a third means for securing a piece of wafer, an adhesive tape, a tape holder and a resilient, flexible component.

DESCRIPTION OF THE PREFERRED EMBODIMENTS

The invention relates to an apparatus for measuring the adhesion, specifically the peeling force and rate of peeling, of a film to a substrate. The present invention will be described in detail with reference to the accompanying drawings. The apparatus includes a means for measuring the peeling force, a means for measuring the rate of peeling, a means for securing a piece of wafer or a wafer, a biasing unit and an adhesive tape. Each of these components will now be described in detail.

Figure 4:
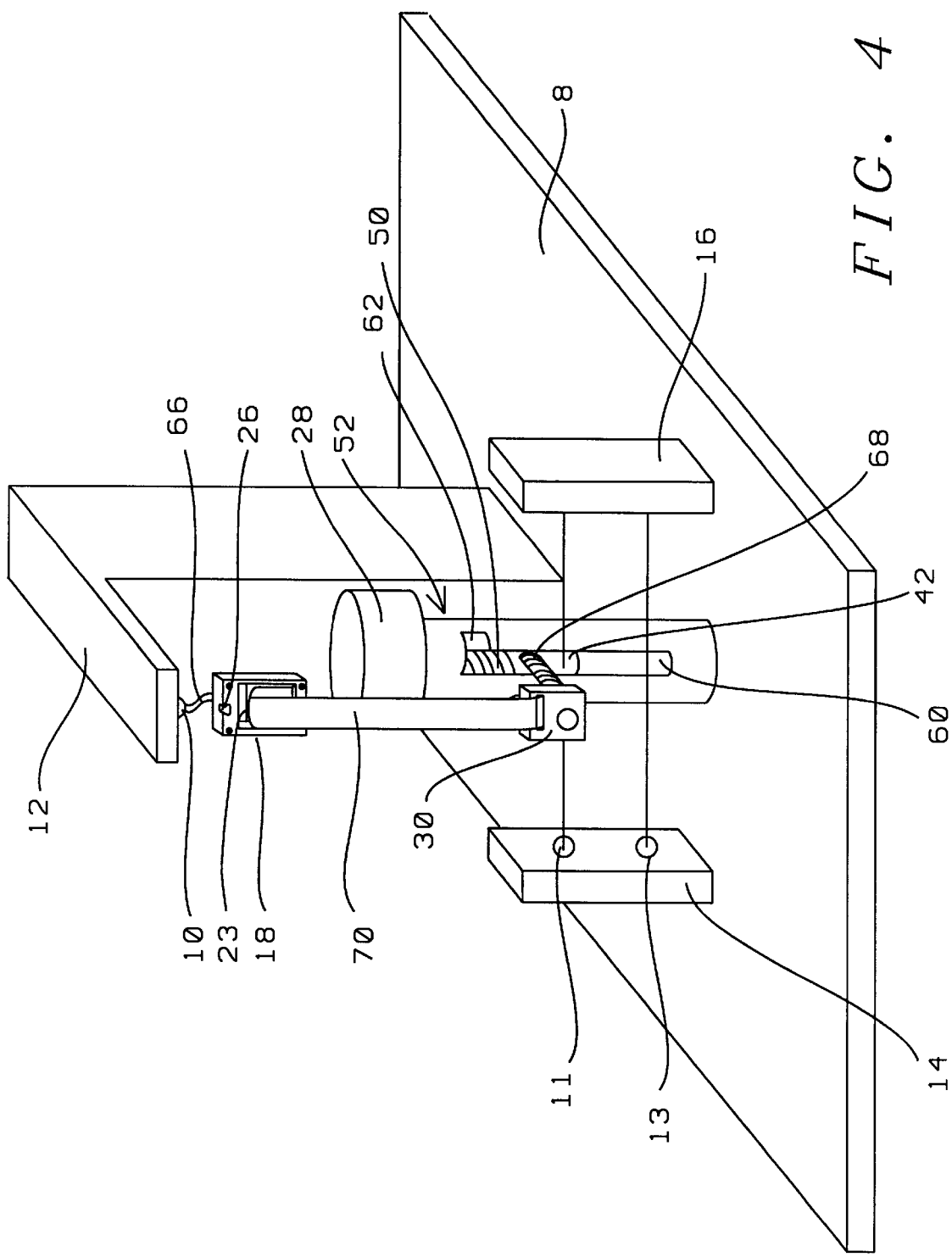
FIG. 4 is a three dimensional view of the apparatus of the invention, the apparatus being completely assembled and moving to the "rest" position.

First will be discussed the means for measuring the peeling force. In the present invention, the means for measuring the peeling force in this invention includes a load cell 10, FIG. 4, and secondary means or components to display the measurement. A portion of the support structure 12, FIG. 4, provides attachment to the load cell 10. Although shown as an inverted L shape, the support structure 12 can also be of other forms, for example an inverted U shape. The signal from the load cell 10 is sent to an amplifier (not shown), the latter then sends the amplified signal to a digital oscilloscope (not shown). The waveform is displayed on the digital oscilloscope, the voltage values of the waveform can in this manner be determined from either the x-axis or the y-axis. This voltage (in volts) can be easily converted into a force (in Newtons). It is also understood that the amplifier and the oscilloscope are only two of the possible means that can be used to translate the pulling force into a form that can be displayed; other devices to achieve the same objective are known in the art and can also be used to perform the same function.

Next will be discussed the means for measuring the rate of peeling of the tape, see FIG. 4. In the present invention, the means to measure the rate of the peeling force includes a beam emission system 14 (FIG. 4), a sensor system 16 (FIG. 4), a means for supplying energy to the beam emission system (not shown), a means for supplying energy to the sensor system (not shown) and a means for computing the time between when the upper emission outlet 11, FIG. 4, is blocked and when the lower emission outlet 13, FIG. 4, Is blocked (not shown). The beam emission system has an upper emission outlet 11 and a lower emission outlet 13, wherein the upper emission outlet 11 and the lower emission outlet 13 are positioned at least 10 millimeters apart from each another. The emission source (not shown) includes but is not restricted to laser or infrared sources. The emission source simultaneously emits a beam through the upper emission outlet 11 and through the lower emission outlet 13. The emitted beam has a circular cross section with a beam size of between 1 mm and 10 mm. The sensor system 16 includes but is not restricted to a photodiode array. A multiple (greater than two) of beam emission systems can also be used.

Figures 1A, 1B:
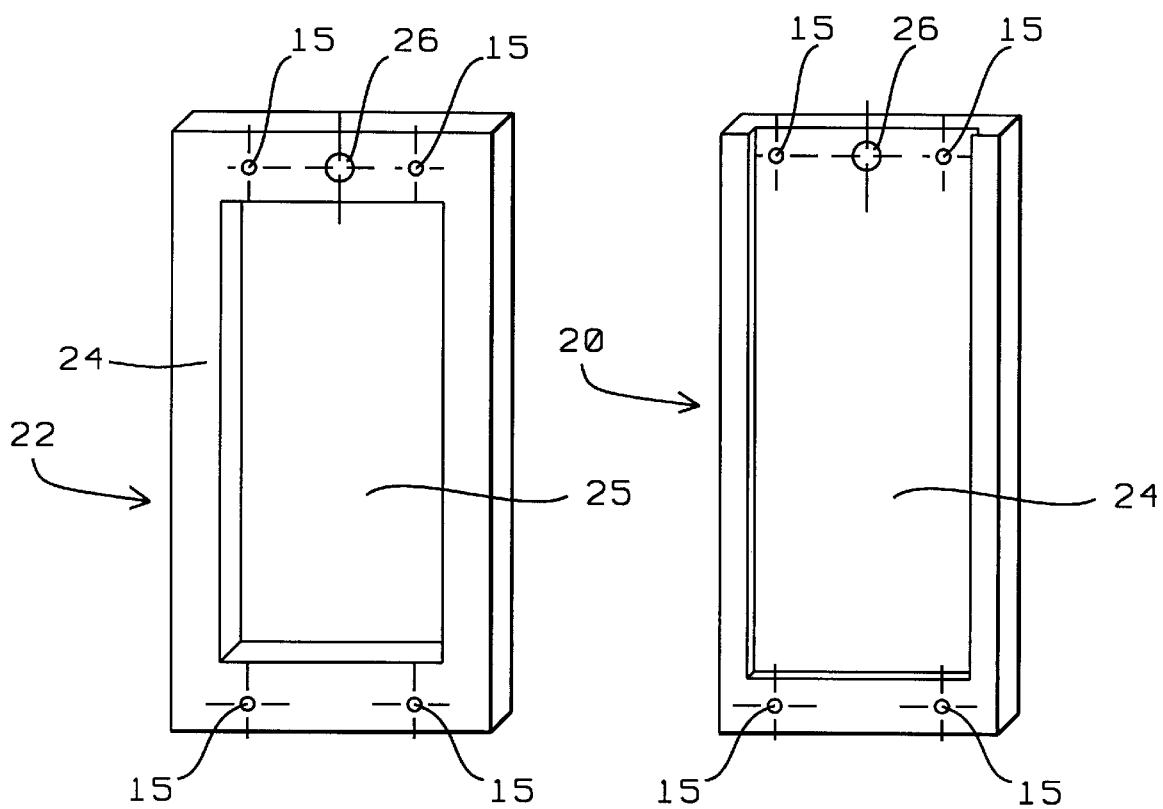
FIG. 1 is a schematic view of the means for securing a piece of wafer, whereby the means comprises two pieces of material 20 and 22.

Next will be discussed the means for securing a piece or fraction of a wafer. The piece or fraction of a wafer containing the film over the substrate needs to be secured in order to facilitate firm positioning (non-movement) during the peeling of the film from the substrate. A means for securing (firmly placing and holding in place) the piece of wafer and at the same time ensuring the absence of wafer cracking and wafer breakage needs to be provided. The means for securing the piece of wafer in this invention is a wafer containment unit 18, FIG. 4, the unit comprising two pieces of material 20 and 22, FIG. 1. As shown in FIG. 1, the first piece of material 20 (hereafter denoted as "wafer holder piece") has a slot 24 such that the piece of wafer is held or contained within the slot 24. The second piece of material 22 (hereafter denoted as "wafer window piece") has an opening 25. The adhering of the adhesive tape 70, see FIG. 4, to the film on the wafer can be achieved through the opening 25, see the combination of the wafer containment unit 18 and the adhesive tape 70 in FIG. 4. While the material for these two pieces includes but is not limited to single metal, metal alloy or plastic, the preferred material in this invention is perspex due to its lightweight. The shape of the wafer holder piece 20 is identical to the shape of the wafer window piece 22 and is preferably rectangle. The slot 24 in the wafer holder piece is machined such that the remaining or un-removed part has the form of a symmetrical U-shape or an asymmetrical U-shape and such that only a portion of the thickness of the material inside the symmetrical U-shape, is removed. Thus an indentation 24 is present against a back portion of the wafer holder 20. The height of the indentation 24 of the wafer holder piece 20 must be of the same thickness as the wafer window piece 22 or greater than the thickness of the wafer window piece 22. The opening 25 in the wafer window piece 22 is machined such that:

(i) the area of the opening 25 in the wafer window piece, FIG. 1, is small relative to the area of the indentation in the wafer holder piece 20
(ii) the opening 25 is wide enough to accommodate the width of the adhesive tape (not shown)
(iii) the length of the opening 25 is at least 5 mm longer than the designated length for the adhesion of the adhesive tape to the exposed wafer piece
(iv) the distance from the bottom edge of the opening 25 in the wafer window piece 22 to the bottom edge of the opening 25 in the wafer window piece 22 is preferably greater than the distance from the bottom edge of the wafer holder piece 20 to the edge of the indentation 24 in the wafer holder piece 20
(v) the distance from the left side edge of the window 25 in the wafer window piece 22 to the left side edge of the opening 25 in the wafer window piece 22 is preferably greater than the distance from the left side edge of the wafer holder piece 20 and the left side edge of the indentation 24 in the wafer holder piece 20
(vi) the same as (v) above except that the requirement applies to the right side edge of the wafer holder piece 20 and the right side edge of the indentation 24 in the wafer holder piece 20.

Referring again to the wafer window 25, FIG. 1, a cushioning material (not shown) such as sponge or bleeding cloth, attached to unit 22 along the outside perimeter of the opening 25 where unit 22 makes contact with the wafer holder piece 20. The cushioning material prevents wafer cracking and wafer breakage during the connection of the wafer holder piece 20 and the wafer window piece 22. Both wafer holder piece 20 and wafer window piece 22 have four holes 15 drilled at the corners and also a fifth hole 26 located mid-way between the two holes 15 at the top of these two pieces 20 and 22. The four holes 15 at the corner have screws fitted through them. For a rectangular piece, the latter hole 26 is preferably situated between two holes 15 along the shorter length of both the wafer holder piece 20 and the wafer window piece 22. The five holes 15/26 in the wafer holder piece 20 are to be aligned to the five holes 15/26 in the wafer window piece 22. The holes 15 are preferably drilled at an equidistant apart from the vertical centerline. The location of the holes 15 should preferably be at a position that allows maximum clamping by the four screws between the wafer holder piece 20m and the wafer window piece 22. The two pieces 20 and 22 form, when screwed together, the wafer containment unit 18 shown in FIG. 4.

The assembly of the means for securing the wafer piece (the wafer containment unit 18, FIG. 4) is now described. It should be understood that the sequence of assembly described hereafter is not the only way but a typical way.

A suitably cut piece of wafer (not shown) containing a film or a multitude of films deposited over the substrate of the wafer (not shown) is placed into the slot 24 of the wafer holder piece 20, wherein the film or a multitude of films on the piece of wafer align opposite to the flat portion 24 of the wafer holder piece 20. The film includes but is not limited to insulators, conductors, semiconductors, porous materials and non-porous materials. The substrate includes but is not limited to monocrystalline silicon, silicon-on-insulator (SOI) and silicon-on-sapphire (SOS). The substrate can further include microelectronic devices and interconnect structures. The wafer window piece is placed over the wafer piece and the wafer holder piece. Upon alignment of the four holes at the corner, screws are then applied to secure the wafer holder piece 20 to the wafer window piece 22, forming the wafer containment unit 18, FIG. 4.

The means for the securing of a wafer or a wafer piece as described above should not be seen as limiting. It can be seen that alternative ways to secure a wafer or a wafer piece can be used. As one alternative, clips can be used instead of screws to secure the wafer holder piece 20 to the wafer window piece 22. As another alternative, the wafer holder piece can be cut to the proper dimensions and then adhered to a support piece of material. As yet another alternative, a wafer in its entirety (without being cut to pieces) can also be secured. As yet one more alternative, the remaining portion in the wafer holder piece can take the form of a 0-shape instead of a U-shape.

It is also necessary to provide an incision into the film or a multitude of films, the incision penetrating into the substrate of the wafer and parallel to the bottom edge of the opening 25 in the wafer window piece 22.

Next will be discussed the means for generating and releasing a resilient deformation. A key aspect of the invention is the creation of a resilient deformation such that a latent or potential pulling force exists for the peeling of the film away from the substrate of the wafer piece to which the film is attached. In this invention, the means for generating and subsequently releasing the resilient deformation is a biasing unit, see FIG. 2.

Figure 2:
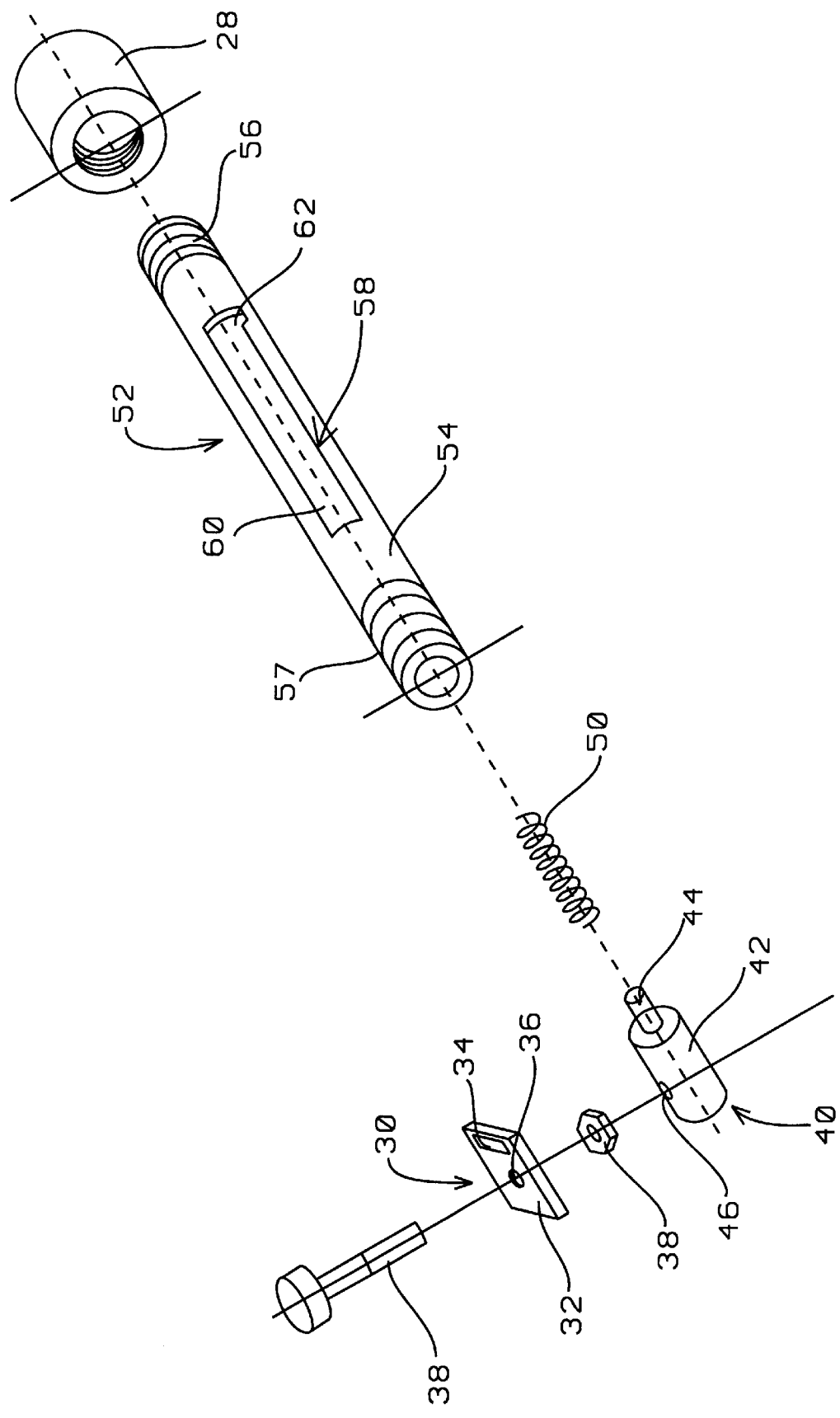
FIG. 2 is a schematic view of the components of the means for generating and releasing a resilient deformation.

FIG. 2 shows the components of the biasing unit, the components include a cap 28, a tape holder 30, a bolt and nut assembly 38, a pusher 40, a compression spring 50 and a hollow cylinder 52. Comparing the components that are shown in FIG. 2 with the assembled apparatus that is shown in FIG. 4 readily leads to an understanding of how the biasing unit of FIG. 2 fits into the assembled apparatus.

The cap 28 comprises a body of material that has a threaded hole drilled partially into the body of material. The material for the cap 28 includes but is not restricted to single metal, metal alloy or plastic. It is preferred that the material of the cap comprises stainless steel due to its toughness and strength. The cap 28 is not limited to any particular shape, but the shape has to be one in which a firm grip (of for instance fingers, for manual attachment) can be obtained during the fastening of the cap 28 to the hollow cylinder 52, FIG. 2.

The tape holder 30, FIG. 2, comprises a plate 32 through which a slit 34 and a hole 36 are drilled. The plate 32 can be of any shape but is preferably a square or rectangle. The material for the plate includes but is not restricted to single metal, metal alloy or plastics. In this invention, aluminum is the preferred material due to its lightweight. There are no limitations on the dimensions and shape of the slit 34, provided that the dimensions and shape allow an adhesive tape (such as tape 70, FIG. 4) to pass through and allow the adhesive part of the adhesive tape to uniformly contact the surface of the slit 34. It is thus preferred that the slit 34 has a length and width wherein the length is longer than the width.

The material of the bolt and nut assembly 38 includes but is not restricted to single metal, metal alloy or plastic. In this invention, the bolt and nut assembly is preferably comprised of stainless steel because of its mechanical strength.

The pusher 40 comprises a first cylindrical part 42 and a second cylindrical part 44, the first cylindrical part 42 being joined to the second cylindrical part 44 and aligned with the first cylindrical part 42 along an axis. The first cylindrical part 42 further has a larger diameter than the second cylindrical part 44, while the first cylindrical part 42 has a threaded hole 46 that is perpendicular to its axis. The threaded hole 46 is partially drilled and threaded into the larger diameter cylindrical part 42. The material for the pusher 40 includes but is not limited to single metal, metal alloy or plastic. Brass is the preferred material for the pusher because of its mechanical strength.

The spring 50 possesses the property of being resilient and flexible. The spring is composed of but not limited to music wire.

The hollow cylinder 52, FIG. 2, comprises a main body 54, two sets of threads 56 and 57, and an opening 58. The two sets of threads 56 and 57 are located at both ends of the main body 54. The material for the hollow cylinder includes but is not restricted to single metal, metal alloy or plastic. It is preferred that the material for the hollow cylinder is stainless steel due to its mechanical strength and ability to resist corrosion. The inner diameter of the hollow cylinder 52 is larger than the diameter of the first cylindrical part 42 of the pusher 40 and spring 50 by about 0.5 mm and 50 mm. The opening 58 of the hollow cylinder 52 comprises a first slit 60 and a second slit 62. The first slit 60 runs parallel or substantially parallel with the axis of the main body 54 of the hollow cylinder 52. The second slit 62 interconnects with the first slit 60 and is perpendicular or substantially perpendicular to the lengthwise dimension of the first slit 60 and intersects the first slit 60 at the end of the first slit 60, thus creating an "L" shaped opening or a mirror image of an "L" shaped opening. The present invention uses a mirror image "L" shaped opening. Alternatively, the second slit 62 can intersect with the first slit 60 perpendicularly or substantially perpendicularly at any point along the length of the first slit 60. In another alternative, a plurality of slits that intersects with the first slit 60 and that are perpendicular or substantially perpendicular to the first slit 60 can also be used. In yet another alternative, the opening 58 has only the first slit 60.

Figure 3:
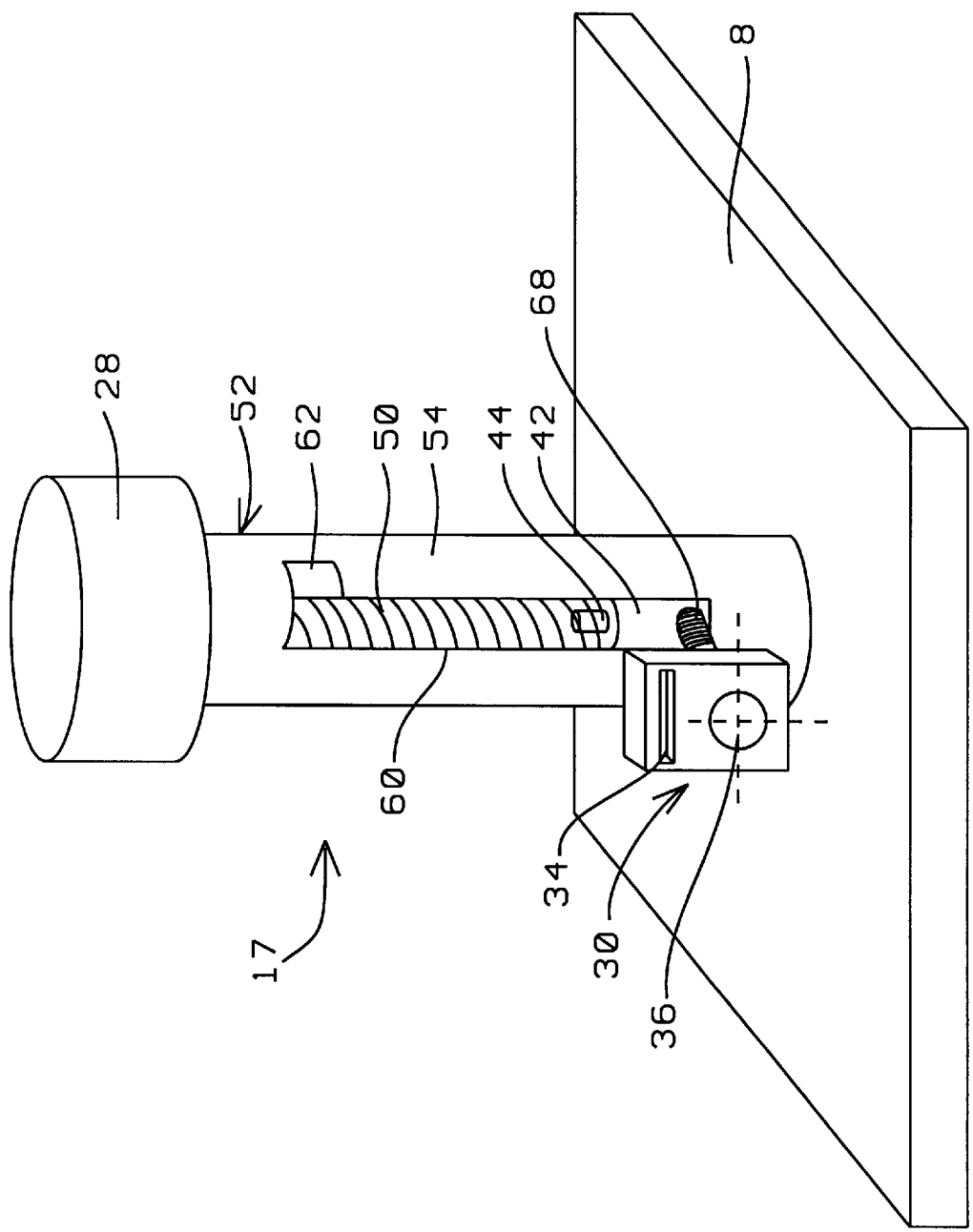
FIG. 3 is a three dimensional view of the means for generating and releasing a resilient deformation or a biasing unit, the means being completely assembled and in a "rest" position.

Next to be discussed is the assembly of the biasing unit 17, FIG. 3. FIG. 3 is a three-dimensional drawing that shows the completed assembly of the biasing unit 17 using the previously described components. The assembly of the biasing unit 17, FIG. 3, will now be described with the understanding that the sequence of assembly described hereafter is not the only possible sequence but is highlighted as a typical method.

The cap screw 28, FIG. 3, is screwed into the thread 56 of the main body 54 of the hollow cylinder 52, that is the thread 56 located at the end of the hollow cylinder 52 that is close to the second slit 62 of the opening 58 in the hollow cylinder 52. The spring 50 is introduced into the hollow cylinder 52 through the opposite open end of the hollow cylinder 52. The pusher 40, wherein the diameter of the larger first cylindrical part 42 is smaller than the inner diameter of the tube 52, is placed inside the main body 54 of the hollow cylinder 52. The placement of the pusher 40 is such that:

(i) the (smaller diameter) second cylindrical part 44 of the pusher 40 is first pushed through the open end of the hollow cylinder 52 that is not capped by cap 28 and that is furthest removed from the second slit 62, (ii) the spring 50 rests on or is slightly compressed by the shoulder of the (larger diameter) first cylindrical part 42 of the pusher 40

(iii) the threaded hole 46 (in first cylinder part 42) is preferably aligned with the opening 58 of the hollow cylinder 52.

The bolt of the bolt and nut assembly 38, FIG. 2, is now put through the hole 36 of the tape holder 30, the nut of the bolt and nut assembly 38 is then screwed into the bolt to secure the plate 32, as yet this optionally allows minimal free rotation of the plate 30 around the bolt 38. The bolt of the bolt and nut assembly 38 in the tape holder 30 is screwed into the threaded hole 46 of the pusher 40. A complete screw into the threaded hole 46 leaves a length 68 of the bolt between the pusher and the nut exposed. The length 68 has to be greater than the beam size of the emission beam (typically between 1 millimeter and 4 millimeters), and is preferably greater than 8 millimeters.

The last step in the assembly of the biasing unit involves the screwing of the remaining open end of the hollow cylinder 52 to the base 8, FIG. 3. Upon assembly, the bolt through opening 36, FIG. 3, that joins the tape holder 30 and the pusher 40, rests on that end of the first slit 60 that is furthest removed from the second perpendicular slit 62. This constitutes the "rest" position, which is shown in FIG. 3.

The tape holder 30, along with the bolt and nut assembly 38 and the pusher 40, is pushed from the end of the first slit 60 in the main body of the hollow cylinder 52 into the second slit 62 (perpendicular to the first slit 60) in the main body. The action constitutes a movement from a previous "rest" position to a "ready" position. The action also actuates the compression of the spring 50, thereby generating the resilient deformation. Upon the movement of the tape holder 30 along with the bolt and nut assembly 38 and the pusher 40 into the first slit 60, the spring 50 instantaneously releases its compression, thereby releasing the resilient deformation.

The means for generating and releasing the resilient deformation is not limiting. Alternatively, a support structure, for example a metal rod, can be placed under a portion of the length 68. The support structure thereafter mechanically or manually lifts the length 68 (along with the tape holder and the pusher) from the "rest" position to the "ready" position, thereby generating the resilient deformation in the compressed spring 50. The same support structure can also be retracted mechanically or manually to actuate the movement from the "ready" position to the "rest" position, thereby releasing the resilient deformation. In this alternative, the opening 58, FIG. 2, in the hollow cylinder can comprise only the first slit 60. In another alternative, a second opening can be created in the hollow cylinder 52, the second opening being opposite to the first opening 58 and the first opening and the second opening having only single, rectangular slits (as opposed to the first slit 60 and the second slit 62 that are shown in FIG. 2). A support structure, for example a metal rod, can be inserted through the second opening, engaging the bottom of the pusher and lifting the pusher (along with the tape holder and the pusher) mechanically or manually from the "rest" position to the "ready" position. The same support structure can also be retracted mechanically or manually to actuate the movement from the "ready" position to the "rest" position. In yet another alternative, compressed air or pneumatic means can be used to generate and release the resilient deformation of the spring. A piston can be optionally placed beneath the (larger diameter) first cylindrical part 42 to allow the compressed air to flow in.

The integration and operation of the apparatus of the invention will next be discussed. FIG. 4 shows the completed assembly of the apparatus wherein the means for generating and releasing a resilient deformation (the biasing unit) shows the tape holder 30 along with the bolt and nut assembly (not highlighted) and the pusher (not highlighted) moving toward the end of the first slit (not highlighted) in the hollow cylinder 52. The assembly or integration of the apparatus is now be described whereby it must be understood that the sequence of the assembly described hereafter is not the only possible method but represents a typical method.

A hook 66, extending from the load cell 10, connects the load cell 10 to the wafer containment unit 18 by hooking into the fifth hole 26 that is (as shown in FIG. 1) midway between the two top corner holes 15. An adhesive tape 70, commercially available (for example 3M#602), is prepared to a designated or predetermined length (about 200 millimeters). The adhesive tape 70 is preferred to have adhesive properties on one side, although adhesive ability on both sides can also be used. A portion of the adhesive tape, preferably the end, is attached to the wafer piece starting exactly at the incision 23 near the bottom of the opening 25 of the wafer containment unit (see FIG. 1). Incision 23 is a cut in the film that is on the surface of the wafer or the wafer sample.

The incision 23 is provided to ensure that the peeling of the film starts at a consistent location, that is the location of the incision, for all tests.

This is followed by cutting the adhesive tape 70 to a predetermined length, which is typically 75 millimeters in accordance with the ASTM test method D3359. However, the predetermined length is not limited to 75 millimeters and can be a length that is smaller than or larger than 75 millimeters, provided that the chosen length is maintained for all tests within a test sequence that are conducted on the apparatus of the invention. After the tape has been cut to the predetermined length, the remainder of the adhesive tape is directed away from the wafer containment unit 18 under an angle of about 180 degrees and towards the tape holder 30, the tape holder 30 (see FIG. 4) is located underneath the wafer containment unit 18. The adhesive part of the adhesive tape that is not adhering to the piece of wafer is thus facing away from the wafer containment unit 18. The adhesive tape 70 then goes through the slit 34 in the tape holder 30 in one of two possible ways:

(i) the adhesive tape goes through the slit 34 with the nonadhesive part contacting the upper part of the slit 34 and, after the tape has passed through the slit and being wrapped upwards in the direction of the wafer containment unit 18, attaching a portion of the adhesive part to the non-adhesive part of the adhesive tape that is located above (that is in the direction of the wafer containment unit 18) the slit, (ii) the adhesive tape goes through the slit 34 with the adhesive part adhering uniformly to the upper part of the slit and, after the tape has passed through the slit and being wrapped upwards in the direction of the wafer containment unit 18, attaching a portion of the adhesive tape to the adhesive part of the adhesive tape that is located above the slit. This is the preferred method.

Upon completion of the attachment of the adhesive tape 70 to the wafer piece (not shown) that is mounted in the wafer containment unit 18 and the connection of the tape 70 to the tape holder 30, it is important to ensure that the adhesive tape 70 is taut and that pre-tension is exerted on the tape 70 in a lengthwise direction of the adhesive tape 70. Tape 70 must be attached such that the tape is stretched tight. If the adhesive tape 70 is not stretched tight, the force that is applied to pull the film away from the substrate is reduced accordingly. For instances where the tape has not been attached in a tight manner and sagging of the tape occurs, the tape must be re-attached to the wafer and the sagging must be eliminated. For tape attachment, the tape can be attached such that a small, pre-determined tension is applied to the tape. The load cell can be calibrated (zeroed) before the tape is mounted.

The means for measuring the rate of peeling force and the means for measuring the peeling force are activated.

After the tape has been attached between the wafer piece (that is mounted in the wafer containment unit 18) and the tape holder 30 as described above, the tape holder 30 (and with that the thereto attached bolt and nut assembly 38) is moved upwards (towards the cap 28 that has been affixed to one end of the hollow cylinder 52), the hollow cylinder 52 is rotated such that the bolt of the bolt and nut assembly 38 enters the second slit 62 that has been provided in the hollow cylinder as previously highlighted. This rotation of the hollow cylinder 52 does not affect the planarity of the mounted tape, in other words the front surface of the wafer containment unit 18, the front surface of the tape holder 30 and the surface of the tape 70 that is stretched between these two latter units are contained in surfaces that are essentially parallel such that the tape 70 is not warped in any way. After the bolt of the bolt and nut assembly has entered the first slot 62, it must be assured that no sagging of the tape occurs since the presence of sagging would make the following measurements unpredictable. The bolt of the bolt and nut assembly 38 keeps the tape holder 30 in place with respect to the wafer containment unit 18, in this manner establishing the initial conditions for the measurements as they are performed using the apparatus of the invention. Rotating the cylinder 52 in the opposite direction will free the bolt of the bolt and nut assembly 38 from slot 62.

The tape holder 30 is moved away from the end of the second slit 62 towards the first slit 60. The moment the bolt of the tape holder 30 enters the first slit 60, the bias of the resiliently deformed spring 50 pushes the pusher 40 and the tape holder 30 downward (towards platform 8) and toward the end of the first slit 60. Since the adhesive tape 70 has been inserted into the slit 34 in the tape holder 30, the tensional force of the spring 50 also pulls the portion of the adhesive tape 70 that is adhered to the film on the wafer piece (not shown). The film that is adhered to the adhesive tape is, as a result, delaminated from the wafer. At the same time, the means for measuring the peeling force (load cell) captures the downward peeling force as the film is being delaminated or pulled away from the substrate. The peeling force in units of voltage is then displayed on a component of the means for measuring the peeling force (for example an oscilloscope). The voltage can then be converted by a component within the means for measuring the peeling force (for example, software) into Newtons and the peeling force in Newtons can be displayed on a component of the means for measuring the peeling force. The adhesion of the film in terms of the peeling force has thus been measured quantitatively.

The adhesion of the film can also be measured quantitatively by the rate of peeling in units of mm/sec or mm/min using the means for measuring the rate of peeling (beam emission system 14, sensor system 16 and other means). The moment the bolt of the tape holder enters the first slit 60, the bias of the resiliently deformed spring pushes the pusher 40 and the tape holder 30 toward the end of the first slit 60. Prior to reaching the end of the first slit 60, the bolt in the tape holder intersects the upper beam (emitted through opening 11, FIG. 4) from the beam emission system 14, and then intersects the lower beam (emitted through opening 13, FIG. 4) from the beam emission system 14. The sensor then registers the time taken to traverse from the upper beam to the lower beam, herein designated as "traversing time".

The rate of peeling is then calculated from the formula:

Distance between the two beam emissions (millimeters)/traversing time (seconds or minutes). Alternatively, the adhesion of the film can also be measured quantitatively by measuring the traversing time, (referring to the above described motion) of the distance between the two beam emissions.

Although the rate of peeling and the peeling force are quantitatively measured in this invention, an alternative embodiment provides for only the rate of peeling or the peeling force to be measured quantitatively. Hence the apparatus for quantitatively measuring the rate of peeling but not the peeling force does not have the means for measuring the peeling force. Similarly, the apparatus for quantitatively measuring the peeling force but not the rate of peeling does not have the means for measuring the rate of peeling. Obviously, many other modifications and variations of the present invention are possible in the light of the above teachings. It is therefore to be understood that within the scope of the appended claims that the invention may be practiced otherwise than as specifically described.

Although the invention has been described and illustrated with reference to specific illustrative embodiments thereof, it is not intended that the invention be limited to those illustrative embodiments. Those skilled in the art will recognize that variations and modifications can be made without departing from the spirit of the invention. It is therefore intended to include within the invention all such variations and modifications which fall within the scope of the appended claims and equivalents thereof.

What is claimed is:

1. An apparatus for quantification of a peeling force required to remove a film deposited over a semiconductor surface from that surface and for the quantification of a rate of peeling during removal of a film deposited over a semiconductor surface, the apparatus comprising:

a base having a first surface and a therewith substantially parallel second surface, said first surface forming an interface on which said apparatus rests and to which no components are attached, said second interface serving as a platform on which components of said apparatus are mounted;

a support structure having an "L" shaped cross section, a longer length of said "L" shaped cross section being mounted perpendicularly to the second surface of said base, a shorter length of said "L" shaped cross section being parallel with said second surface of said base and extending above the second surface of said base over a measurable distance;

a load cell, having been provided with an unmoving first attachment attaching said load cell in a fixed position to said shorter length of said "L" shaped support structure, said load cell facing said second surface of said base, said load cell further having been provided with a movable second attachment facing said second surface of said base, said load cell providing a measurement of a force which equals said peeling force being exerted on said second movable attachment of said load cell, said first attachment of said load cell being attached in a fixed position to said shorter length of said "L" shaped support structure, said force being essentially parallel with said longer length of said "L" shaped support structure;

a wafer containment unit into which a wafer or a portion thereof is firmly mounted while providing a window therein for access to a surface of said mounted wafer or a portion thereof, said wafer containment unit being attached to said second attachment of said load cell in a direction towards said second surface of said base, said window in said wafer containment unit facing a direction being parallel with said second surface of said base;

a hollow cylinder mounted on said second surface of said base within which is mounted a spring on a surface of a cylindrical part, said cylindrical part having been provided with a threaded opening in sidewalls thereof, said hollow cylinder further having been provided with a cut-out in walls of said hollow cylinder;

a tape holder having been provided with a slit for tape insertion and an opening through which a nut-and-bolt assembly is mounted, said bolt protruding from said tape holder in a direction of said cut-out in a wall of said hollow cylinder and extending over a distance allowing said bolt of said nut-and-bolt assembly being inserted into said cut-out in a wall of said hollow cylinder, thereby enabling said bolt being threaded into said threaded opening provided in said cylindrical part mounted inside said hollow cylinder, said bolt contacting and being able to manipulate said cylindrical part and therewith said spring in a center of said hollow cylinder, allowing said cylindrical part and therewith said spring in the center of said hollow cylinder to be mounted in a compressed position by inserting said bolt in a portion of said cut-out in said wall of said hollow cylinder, from which position said bolt and therewith said cylindrical part and said spring are released, thereby releasing tensile strength contained in said spring, said bolt of said bolt-and-nut assembly partially protruding in a direction from said hollow cylinder, said bolt of said bolt-and-nut assembly keeping said tape holder in place adjacent to said hollow cylinder, said slot in said tape holder facing away from said second surface of said base and towards said wafer containment unit;

a tape having at least one adhesive surface connected between said wafer or a portion thereof being accessible through said window in said wafer containment unit and said slot in said tape holder;

a beam emission system and a therewith functionally connected beam sensor system with both systems mounted on said second surface of said base, both systems being provided with upper and lower beam outlets whereby the upper outlets of the beam emission system are aligned with the upper outlets of the beam sensor system and the lower outlets of the beam emission system are aligned with the lower outlets of the beam sensor system, whereby beams emitted from said emission system travel to said sensor system in a direction perpendicular to said direction in which said bolt of said nut-and-bolt assembly protrudes from said hollow cylinder through said cut-out in walls of said hollow cylinder, said partial protrusion of said bolt from said hollow cylinder being able to interrupt a beam travelling between said beam emission system and said sensor system, therewith providing ability to measure time between an object passing between said upper outlets and said lower outlets of said beam emission system and said beam sensor system, thereby measuring said rate of peeling.

2. The apparatus of claim 1, this apparatus being limited to measuring a peeling force required to remove a film deposited over the surface of a substrate.

3. The apparatus of claim 1, this apparatus being limited to measuring a rate of peeling during removal of a film deposited over the surface of a substrate. 4.

4. The apparatus of claim 1, said semiconductor surface being selected from the group of surfaces consisting of semiconductor substrates, including monocrystalline silicon, silicon-on insulator (SOI), silicon-on-sapphire (SOS), printed circuit boards, flex circuits or a metallized or glass substrate or semiconductor device mounting support.

5. The apparatus of claim 1, said film being selected from the group of films consisting of insulators, passivation layers, dielectric layers thereby including inter metal dielectrics and intra-level dielectrics, photoresist, anti-reflective coatings, diffusion barrier layers and seed layers and conductors thereby including metals, silicate, a salicide, poly silicon, amorphous silicon, a polymer, or any other semiconductor compatible conductive layer.

6. The apparatus of claim 1, said beam emission systems and sensor systems being selected from the group consisting of infrared beam systems and laser beam systems.

7. An apparatus for quantification of a peeling force required to remove a film deposited over a semiconductor surface from that surface and for the quantification of a rate of peeling during removal of a film deposited over a semiconductor surface, the apparatus comprising a base plate and an inverted "L" shaped support structure mounted on the surface of said base plate and having a longer leg perpendicular to said base plate and a shorter parallel to said base plate, the apparatus further comprising:

a first means for measuring a peeling force;

a second means for measuring a rate of peeling;

a third means for securing a wafer or piece of wafer, a semiconductor film having been created on the surface of said wafer or piece of wafer;

a fourth means for generating and releasing a resilient deformation; and a fifth means for transferring said resilient deformation from said means for generating and releasing a resilient deformation to said semiconductor film created on the surface of said wafer or piece of wafer.

8. The apparatus of claim 7, said first means for measuring the peeling force comprising a load cell, having been provided with an unmoving first attachment attaching said load cell in a fixed position to said shorter length of said "L" shaped support structure, said load cell facing said base plate, said load cell further having been provided with a movable second attachment facing said base plate, said load cell providing a measurement of a force which equals said peeling force exerted on said second movable attachment of said load cell while said first attachment of said load cell is attached in a fixed position to said shorter length of said "L" shaped support structure, said force being essentially parallel with said longer length of said "L" shaped support structure.

9. The apparatus of claim 7, wherein said second means for measuring the rate of peeling comprising a beam emission system and a therewith functionally connected beam sensor system with both systems mounted on said base plate, both systems being provided with upper and lower beam outlets, the upper outlets of the beam emission system being aligned with the upper outlets of the beam sensor system, the lower outlets of the beam emission system being aligned with the lower outlets of the beam sensor system, beams emitted from said emission system travelling to said sensor system in a direction parallel with the surface of said base plate, thereby being able to interrupt a beam that travels between said beam emission system and said sensor system by a body that travels in a direction perpendicular to the surface of said base plate, therewith providing a means to measure time between an object passing between said upper outlets and said lower outlets of said beam emission system of said beam sensor system, thereby measuring said rate of peeling.

10. The apparatus of claim 7, said third means for securing a wafer or piece of wafer comprising a wafer containment unit into which a wafer or a portion thereof is firmly mounted, providing a window therein for access to a surface of said mounted wafer or a portion thereof, said wafer containment unit being attached to said first means of measuring a peeling force in a direction towards said base plate, said window in said wafer containment unit facing a direction parallel with said base plate.

11. The apparatus of claim 7, said fourth means for generating and releasing a resilient deformation comprising:

a hollow cylinder mounted on said base plate within which is mounted a spring on a surface of a cylindrical part, said cylindrical part having been provided with a threaded opening in sidewalls thereof, said hollow cylinder further having been provided with a cut-out in walls of said hollow cylinder; and a tape holder provided with a slit for tape insertion and an opening through which a nut-and-bolt assembly is mounted, said bolt protruding from said tape holder in a direction of said cut-out in a wall of said hollow cylinder and extending over a distance allowing said bolt of said nut-and-bolt assembly being inserted into said cut-out in a wall of said hollow cylinder, thereby enabling said bolt being threaded into said threaded opening provided in said cylindrical part mounted inside said hollow cylinder, said bolt contacting and being able to manipulate said cylindrical part and therewith said spring in a center of said hollow cylinder, allowing said cylindrical part and therewith said spring in the center of said hollow cylinder to be mounted in a compressed position by inserting said bolt in a portion of said cut-out in said wall of said hollow cylinder, from which position said bolt and therewith said cylindrical part and said spring are released, thereby releasing tensile strength contained in said spring, said bolt of said bolt-and-nut assembly partially protruding in a direction from said hollow cylinder, said bolt of said bolt-and-nut assembly keeping said tape holder in place adjacent to said hollow cylinder, said slot in said tape holder facing away from said base plate and towards said third means of securing a wafer or piece of wafer.

12. The apparatus of claim 7, wherein said fifth means for transferring said resilient deformation from said means for generating and releasing a resilient deformation to said semiconductor film created on the surface of said wafer or piece of wafer comprising an adhesive tape connected to said semiconductor film created on the surface of said wafer or piece of wafer and said fourth means for generating and releasing a resilient deformation.

13. A method for quantification of a peeling force required to remove a film deposited over a semiconductor surface from that surface and for the quantification of a rate of peeling during removal of a film deposited over a semiconductor surface, comprising the steps of:

providing a base having a first surface and a therewith substantially parallel second surface, said first surface forming an interface to which no components are attached, said second interface serving as a platform on which components used for said method of quantification are mounted;

providing a support structure having an "L" shaped cross section with a longer length of said "L" shaped cross section being mounted perpendicularly to the second surface of said base with a shorter length of said "L" shaped cross section being parallel with said second surface of said base and extending above the second surface of said base over a measurable distance;

providing a load cell, having been provided with an unmoving first attachment attaching said load cell in a fixed position to said shorter length of said "L" shaped support structure, said load cell facing said second surface of said base, said load cell further having been provided with a movable second attachment facing said second surface of said base, said load cell providing a measurement of a force which equals said peeling force exerted on said second movable attachment of said load cell, said first attachment of said load cell being attached in a fixed position to said shorter length of said "L" shaped support structure, said force being essentially parallel with said longer length of said "L" shaped support structure;

providing a wafer containment unit into which a wafer or a portion thereof is firmly mounted, providing a window therein for access to a surface of said mounted wafer or a portion thereof, said wafer containment unit being attached to said second attachment of said load cell in a direction towards said second surface of said base, said window in said wafer containment unit facing a direction parallel with said second surface of said base;

providing a hollow cylinder mounted on said second surface of said base within which is mounted a spring on a surface of a cylindrical part, said cylindrical part having been provided with a threaded opening in sidewalls thereof, said hollow cylinder further having been provided with a cut-out in walls of said hollow cylinder;

providing a tape holder provided with a slit for tape insertion and an opening through which a nut-and-bolt assembly is mounted, said bolt protruding from said tape holder in a direction of said cut-out in a wall of said hollow cylinder and extending over a distance allowing said bolt of said nut-and-bolt assembly being inserted into said cut-out in a wall of said hollow cylinder, thereby enabling said bolt being threaded into said threaded opening provided in said cylindrical part mounted inside said hollow cylinder, said bolt contacting and manipulating said cylindrical part and therewith said spring in a center of said hollow cylinder, allowing said cylindrical part and therewith said spring in the center of said hollow cylinder to be mounted in a compressed position by inserting said bolt in a portion of said cut-out in said wall of said hollow cylinder, from which position said bolt and therewith said cylindrical part and said spring is released, thereby releasing tensile strength contained in said spring, said bolt of said bolt-and-nut assembly partially protruding in a direction from said hollow cylinder, said bolt of said bolt-and-nut assembly keeping said tape holder in place adjacent to said hollow cylinder, said slot in said tape holder facing away from said second surface of said base and towards said wafer containment unit;

providing a tape having at least one adhesive surface connected between said wafer or a portion thereof, said tape being accessible through said window in said wafer containment unit and said slot in said tape holder;

providing a beam emission system and a therewith functionally connected beam sensor system, both systems being mounted on said second surface of said base, both systems being provided with upper and lower beam outlets, the upper outlets of the beam emission system being aligned with the upper outlets of the beam sensor system, the lower outlets of the beam emission system being aligned with the lower outlets of the beam sensor system, beams emitted from said emission system travelling to said sensor system in a direction perpendicular to said direction in which said bolt of said nut-and-bolt assembly protrudes from said hollow cylinder through said cut-out in walls of said hollow cylinder, said partial protrusion of said bolt from said hollow cylinder interrupting a beam that travelling between said beam emission system and said sensor system, providing ability to measure time between an object passing between said upper outlets and said lower outlets of said beam emission system and said beam sensor system, thereby measuring said rate of peeling;

positioning said tape between the surface of said film deposited over a semiconductor surface and said slit provided in said tape holder by adhering said tape to said surface and inserting said tape into said slit, said adhering to said surface and inserting into said slit being performed such that said tape is stretched tout and without slack or warping;

placing said spring in a center of said hollow cylinder in a compressed position by inserting said bolt of said bolt-and-nut assembly in a portion of said cut-out in said wall of said hollow cylinder;

releasing said bolt of said bolt-and-nut assembly from its compressed position; and recording said peeling force by recording a reading obtained from said load cell, further recording said rate of peeling force by recording a reading obtained from said beam emission system.

14. The method of claim 13, this method being limited to measuring a peeling force required to remove a film deposited over the surface of a substrate.

15. The method of claim 13, this method being limited to measuring a rate of peeling during removal of a film deposited over the surface of a substrate.

16. The method of claim 13, said semiconductor surface being selected from the group of surfaces consisting of semiconductor substrates thereby including monocrystalline silicon, silicon-on insulator (SOI), silicon-on-sapphire (SOS), printed circuit boards, flex circuits or a metallized or glass substrate or semiconductor device mounting support.

17. The method of claim 13, said film being selected from the group of films consisting of insulators, passivation layers, dielectric layers thereby including inter metal dielectrics and intra-level dielectrics, photoresist, anti-reflective coatings, diffusion barrier layers and seed layers and conductors thereby including metals, silicate, a salicide, poly silicon, amorphous silicon, a polymer, or any other semiconductor compatible conductive layer.

18. The method of claim 13, said beam emission systems and sensor systems being selected from the group consisting of infrared beam systems and laser beam systems.

19. A method for quantification of a peeling force required to remove a film deposited over a semiconductor surface from that surface and a rate of peeling during removal of a film that has been deposited over a semiconductor surface, the method making use of a provided base plate and a provided inverted "L" shaped support structure mounted on the surface of said base plate and having a longer leg perpendicular to said base plate and a shorter parallel to said base plate, the method comprising:

providing a first means for measuring a peeling force;

providing a second means for measuring a rate of peeling;

providing a third means for securing a wafer or piece of wafer, a semiconductor film having been created on the surface of said wafer or piece of wafer;

providing a fourth means for generating and releasing a resilient deformation;

providing a fifth means for transferring said resilient deformation from said means for generating and releasing a resilient deformation to said semiconductor film created on the surface of said wafer or piece of wafer;

enabling said first means for measuring the peeling force and said second means for measuring the rate of peeling by functionally engaging said fifth means with said third means and said fourth means, further functionally placing said fourth means in a position where said fourth means provides said resilient deformation; and performing said measuring the peeling force and measuring the rate of peeling by releasing said resilient deformation from said fourth means and recording said peeling force by recording a reading obtained from said first means, further recording said rate of peeling force by recording a reading obtained from said second means.

20. The method of claim 19, said providing first means for measuring the peeling force comprising providing a load cell, having been provided with an unmoving first attachment attaching said load cell in a fixed position to said shorter length of said "L" shaped support structure, said load cell facing said base plate, said load cell further having been provided with a movable second attachment facing said base plate, said load cell providing a measurement of a force which equals said peeling force exerted on said second movable attachment of said load cell, said first attachment of said load cell being attached in a fixed position to said shorter length of said "L" shaped support structure, said force being essentially parallel with said longer length of said "L" shaped support structure.

21. The method of claim 19, said providing second means for measuring the rate of peeling comprising providing a beam emission system and a therewith functionally connected beam sensor system with both systems being mounted on said base plate, both systems being provided with upper and lower beam outlets, the upper outlets of the beam emission system being aligned with the upper outlets of the beam sensor system, the lower outlets of the beam emission system being aligned with the lower outlets of the beam sensor system, beams emitted from said emission system travelling to said sensor system in a direction parallel with the surface of said base plate, enabling interrupting a beam travelling between said beam emission system and said sensor system by a body that travels in a direction perpendicular to the surface of said base plate, therewith providing a means to measure time between an object passing between said upper outlets and said lower outlets of said beam emission system and said beam sensor system, thereby measuring said rate of peeling.

22. The method of claim 19, said providing third means for securing a wafer or piece of wafer comprising providing a wafer containment unit into which a wafer or a portion thereof is firmly mounted while providing a window therein for access to a surface of said mounted wafer or a portion thereof, said wafer containment unit being attached to said first means of measuring the peeling force in a direction towards said base plate, said window in said wafer containment unit facing a direction parallel with said base plate.

23. The method of claim 19, said providing fourth means for generating and releasing a resilient deformation comprising the steps of:

providing a hollow cylinder mounted on said base plate within which is mounted a spring on a surface of a cylindrical part, said cylindrical part having been provided with a threaded opening in sidewalls thereof, said hollow cylinder further having been provided with a cut-out in walls of said hollow cylinder; and providing a tape holder provided with a slit for tape insertion and an opening through which a nut-and-bolt assembly is mounted, said bolt protruding from said tape holder in a direction of said cut-out in a wall of said hollow cylinder and extending over a distance allowing said bolt of said nut-and bolt assembly being inserted into said cut-out in a wall of said hollow cylinder, enabling said bolt being threaded into said threaded opening provided in said cylindrical part mounted inside said hollow cylinder, said bolt contacting and manipulating said cylindrical part and therewith said spring in the center of said hollow cylinder, allowing said cylindrical part and therewith said spring in the center of said hollow cylinder to be mounted in a compressed position by inserting said bolt in a portion of said cut-out in said wall of said hollow cylinder, from which position said bolt and therewith said cylindrical part and said spring is released, thereby releasing tensile strength contained in said spring, said bolt of said bolt-and-nut assembly partially protruding in a direction from said hollow cylinder, said bolt of said bolt-and-nut assembly keeping said tape holder in place adjacent to said hollow cylinder, said slot in said tape holder facing away from said base plate and towards said third means of securing a wafer or piece of wafer.

24. The method of claim 19, said providing fifth means for transferring said resilient deformation from said means for generating and releasing a resilient deformation to said semiconductor film created on the surface of said wafer or piece of wafer comprising providing an adhesive tape connected to said semiconductor film created over the surface of said wafer or piece of wafer and said fourth means for generating and releasing a resilient deformation.

* * * * *